US011167439B2

(12) United States Patent
Mayer

(10) Patent No.: US 11,167,439 B2
(45) Date of Patent: Nov. 9, 2021

(54) PRECISION SKIVER

(71) Applicant: Todd Michael Mayer, Dayton, MN (US)

(72) Inventor: Todd Michael Mayer, Dayton, MN (US)

(73) Assignee: Mayer Engineering, LLC, Dayton, MN (US)

( * ) Notice: Subject to any disclaimer, the term of this patent is extended or adjusted under 35 U.S.C. 154(b) by 0 days.

(21) Appl. No.: 16/873,334

(22) Filed: Mar. 20, 2020

(65) Prior Publication Data

US 2021/0291393 A1    Sep. 23, 2021

(51) Int. Cl.
  *B26B 21/40* (2006.01)
  *B67B 7/46* (2006.01)
  *B26B 29/06* (2006.01)

(52) U.S. Cl.
  CPC .......... *B26B 21/4062* (2013.01); *B26B 29/06* (2013.01); *B67B 7/30* (2013.01)

(58) Field of Classification Search
  CPC ........ B26B 21/4062; B26B 29/06; B67B 7/30
  USPC .......................................................... 30/289
  See application file for complete search history.

(56) References Cited

U.S. PATENT DOCUMENTS

| 322,304 | A | * | 7/1885 | Mander | B27G 17/04 30/281 |
|---|---|---|---|---|---|
| 1,052,881 | A | * | 2/1913 | Symons | B27G 17/02 30/484 |
| 1,440,649 | A | * | 1/1923 | Tvedt | B27G 17/02 30/489 |
| 2,199,380 | A | * | 5/1940 | Walraven | B23D 29/026 30/168 |
| 2,472,528 | A | * | 6/1949 | Grimes | C14B 1/14 69/20 |
| 2,779,367 | A | * | 1/1957 | Forbes | B23Q 13/00 30/167 |
| 4,001,934 | A | * | 1/1977 | Bell | B26B 27/00 30/124 |
| 4,124,015 | A | | 11/1978 | Isaksson | |
| 4,300,287 | A | * | 11/1981 | Tibbs | B23D 29/005 30/277 |
| 4,592,253 | A | | 6/1986 | Hatfield | |
| 4,628,783 | A | | 12/1986 | Brownell et al. | |
| 5,311,663 | A | | 5/1994 | Garze et al. | |
| 5,419,044 | A | * | 5/1995 | Valliere | B67B 7/30 30/2 |
| 5,577,150 | A | * | 11/1996 | Holder | G02B 6/4475 30/90.4 |
| 5,771,586 | A | | 6/1998 | Lotarski et al. | |
| 5,771,587 | A | | 6/1998 | Herold | |
| 5,865,085 | A | | 2/1999 | Vollenweider | |

(Continued)

FOREIGN PATENT DOCUMENTS

FR    1196492 A  *  11/1959  ............. B27G 17/02

*Primary Examiner* — Kenneth E Peterson
*Assistant Examiner* — Liang Dong
(74) *Attorney, Agent, or Firm* — Laabs Intellectual Property

(57) ABSTRACT

A manual skiver (10) for precise removal of outside material from an elongated device, such as a medical catheter or the like, includes a longitudinal recess (11) in a planar bottom surface (24) at the front end, a transverse replaceable blade (28) therein, a removable cover (32), and a handle (22) extending from the back end thereof. A second embodiment (66) is also disclosed.

18 Claims, 8 Drawing Sheets

(56) References Cited

U.S. PATENT DOCUMENTS

| | | | |
|---|---|---|---|
| 6,751,876 B2 | 6/2004 | Herold | |
| 6,807,737 B1 | 10/2004 | Davia | |
| 7,533,595 B2 * | 5/2009 | Domenico | B26B 3/08 |
| | | | 30/286 |
| 7,735,404 B2 | 6/2010 | Wilk | |
| 8,250,960 B2 | 8/2012 | Hayner et al. | |
| 2004/0040163 A1 * | 3/2004 | Lin | B27G 21/00 |
| | | | 30/478 |
| 2005/0229403 A1 | 10/2005 | Diaz | |
| 2006/0027063 A1 | 2/2006 | Currier et al. | |
| 2012/0311866 A1 | 12/2012 | Jones et al. | |
| 2015/0047207 A1 * | 2/2015 | Chernyshou | B27D 5/006 |
| | | | 30/169 |
| 2016/0097911 A1 * | 4/2016 | George | G02B 6/46 |
| | | | 29/428 |
| 2017/0057115 A1 * | 3/2017 | Keeling | B27G 17/02 |

* cited by examiner

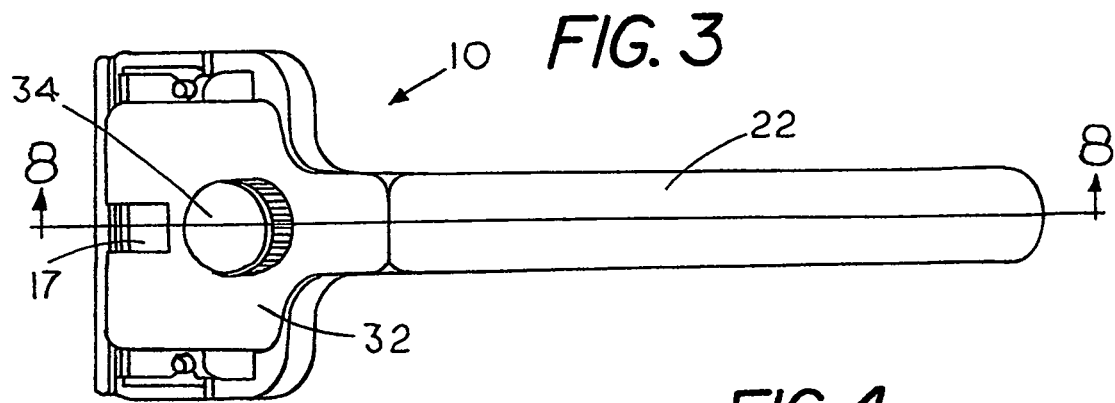
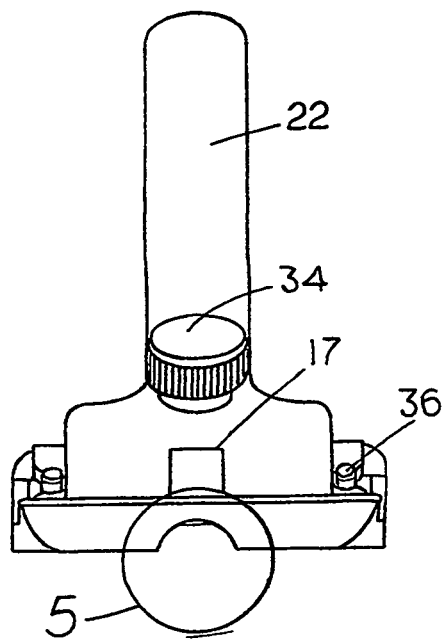
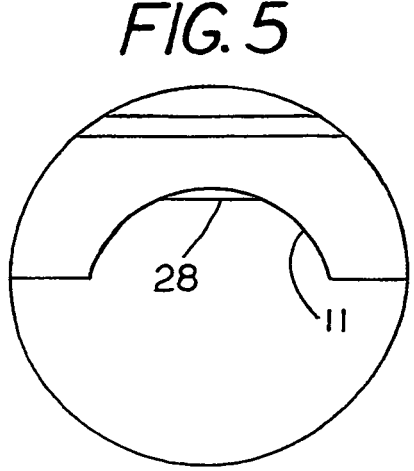
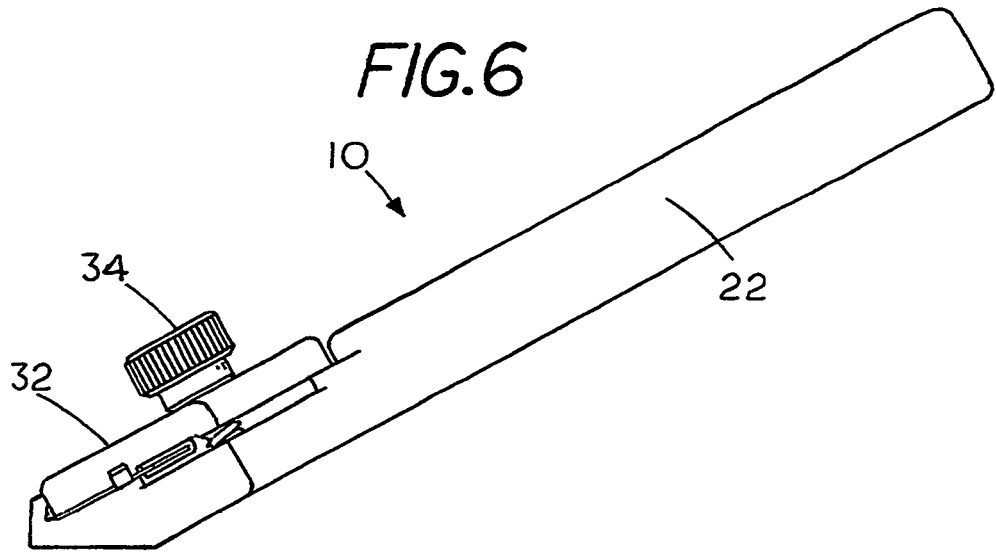

PRECISION SKIVER

TECHNICAL FIELD

The present invention relates generally to manual cutting tools, and more particularly to a new and unique skiver for precisely removing a thin layer of material from the outside of an elongated, tubular object such as a medical catheter.

BACKGROUND OF THE INVENTION

Some products, such as medical catheters, for example, are typically manufactured with a thin outer layer of thermoplastic heat shrink that must be removed before packaging, shipment and then use. Similarly, some batteries are manufactured with such an outside layer to prevent electrical shorting before packaging. Such heat shrink is quite thin and tight on the product.

In the past this outer layer has been removed by carefully holding the product in one hand, making a small cut in the end of the layer to facilitate grasping and then stripping it away with the other hand. This is time consuming and can result in either damage to the product or injury to the hand holding the product.

Although various manual cutting tools for various purposes have been available heretofore, there has not been a tool that is specifically adapted for this purpose while avoiding possible injury to the hand.

U.S. Pat. Nos. 7,533,595 and 5,419,044 are representative of the prior art in this regard. The '595 patent to Domenico shows a lamina cutter. The '044 patent to Valliere shows a cutter for opening relatively thin flat packages such as medical IV bags. Both cutters include recessed blades but are not suited for precise removal of an outer layer of heat shrink tight on a product.

A need has thus arisen for a new and improved skiver for precisely and safely removing a thin layer of heat shrink material from products such as medical catheters, small batteries and the like without risking injury.

SUMMARY OF THE INVENTION

The present invention comprises a new and unique skiver of improved construction which overcomes the foregoing and other difficulties associated with the prior art. In accordance with the invention there is provided a manual skiver with a body attached to the front end of a handle. A longitudinal recess is provided in the lower surface of the skiver body for guiding a catheter or the like past a transverse blade extending into the top of the recess as the skiver is advanced along the length thereof to precisely remove a thin layer of outside material such as plastic heat shrink without damaging the underlying catheter, while being supported either on a flat work surface or a separate mount in order to protect the user from injury.

BRIEF DESCRIPTION OF DRAWING

A better understanding of the invention can be had by reference to the following Detailed Description in conjunction with the accompanying Drawing, wherein:

FIG. 3 is a top view thereof;

FIG. 4 is a front view thereof;

FIG. 5 is a detail view of a portion of FIG. 4;

FIG. 6 is a side view thereof;

DETAILED DESCRIPTION

Figure 1:
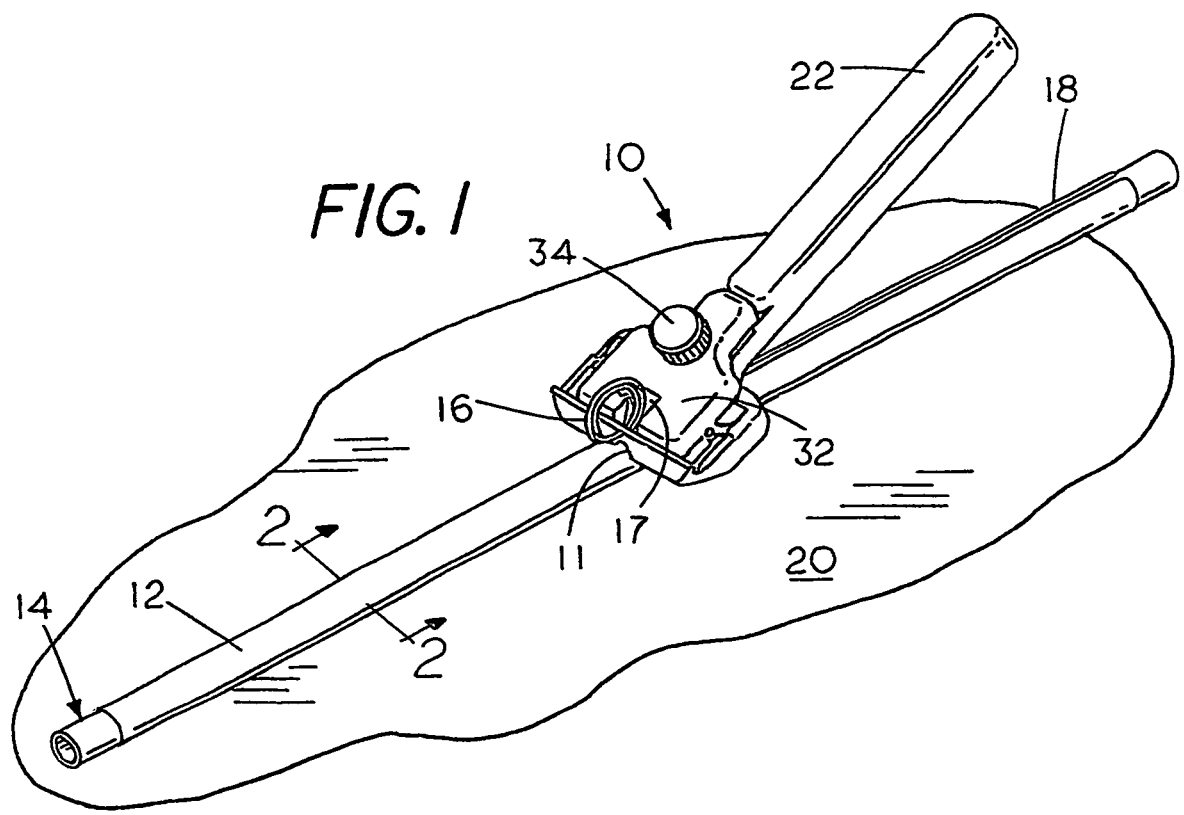
FIG. 1 is a perspective view of the improved skiver according to a first embodiment of the invention herein.
Figure 2:
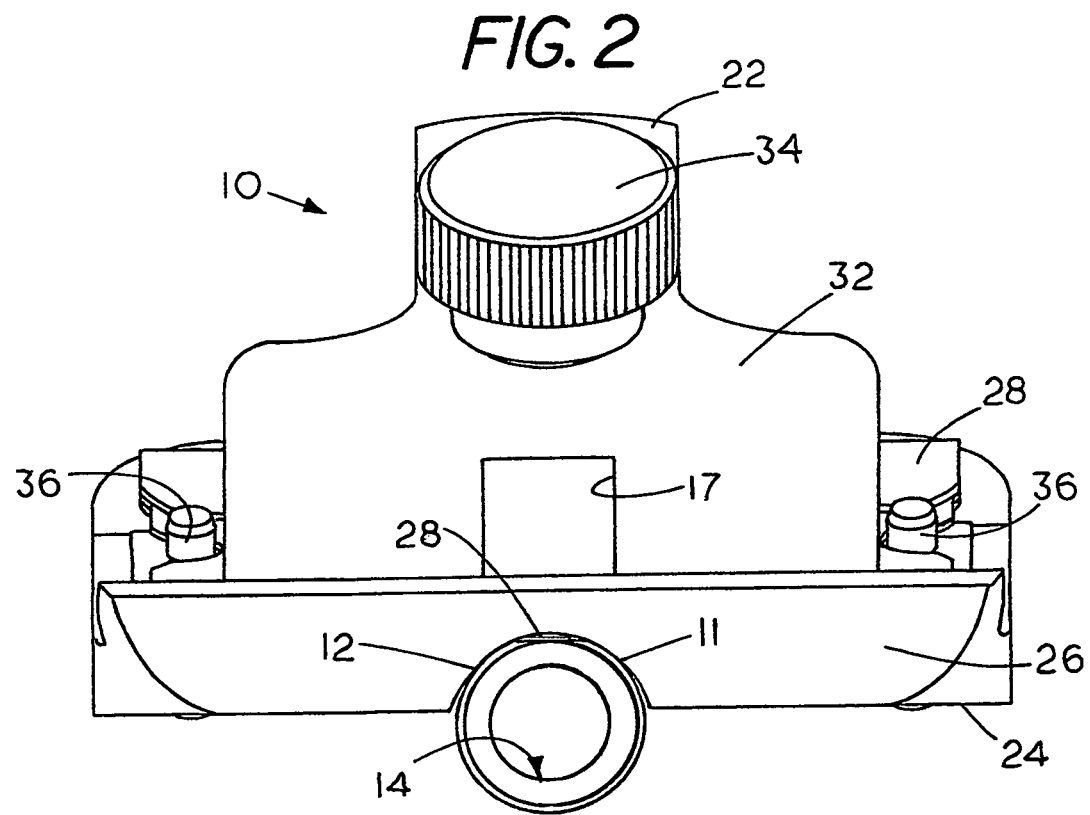
FIG. 2 is an enlarged cross-sectional view taken along lines 2-2 of FIG. 1 in the direction of the arrows.

Referring now to the Drawing, wherein like reference numerals designate like or corresponding elements throughout the views, FIGS. 1-10 show a skiver 10 incorporating a first embodiment of the invention. The skiver 10 can be used to remove a thin layer of material 12, such as plastic heat shrink, from the outside of a catheter 14. A longitudinal recess 11 is provided in the bottom of skiver 10 for receiving the catheter 14. The recess 11 is of semicircular cross section. As the skiver 10 is advanced along its length, the material 12 is removed from catheter 14 in a strip 16 that curls out of an opening 17 in the top of the skiver 10, leaving a longitudinal opening or slot 18 so that the rest of the outer layer of material can then be easily stripped away before packaging of the catheter.

The catheter 14 can be supported either on a flat work surface 20, or in a separate accessory described below, for better precision and in order to avoid possible injury to the user.

The skiver 10 includes a body with handle 22 extending from its back end. The surface of handle 22 is preferably ribbed or textured to facilitate secure gripping by the user. The front end of the body of skiver 10 is relatively wider than handle 22, with a substantially flat or planar bottom surface 24 and an inclined flat front surface 26 in which the longitudinal recess 11 is located. Front surface 26 is preferably angled upward at an acute angle from surface 24. The recess 11 is preferably semi-cylindrical in shape and dimensioned in accordance with the size of catheter 14.

Figure 9:
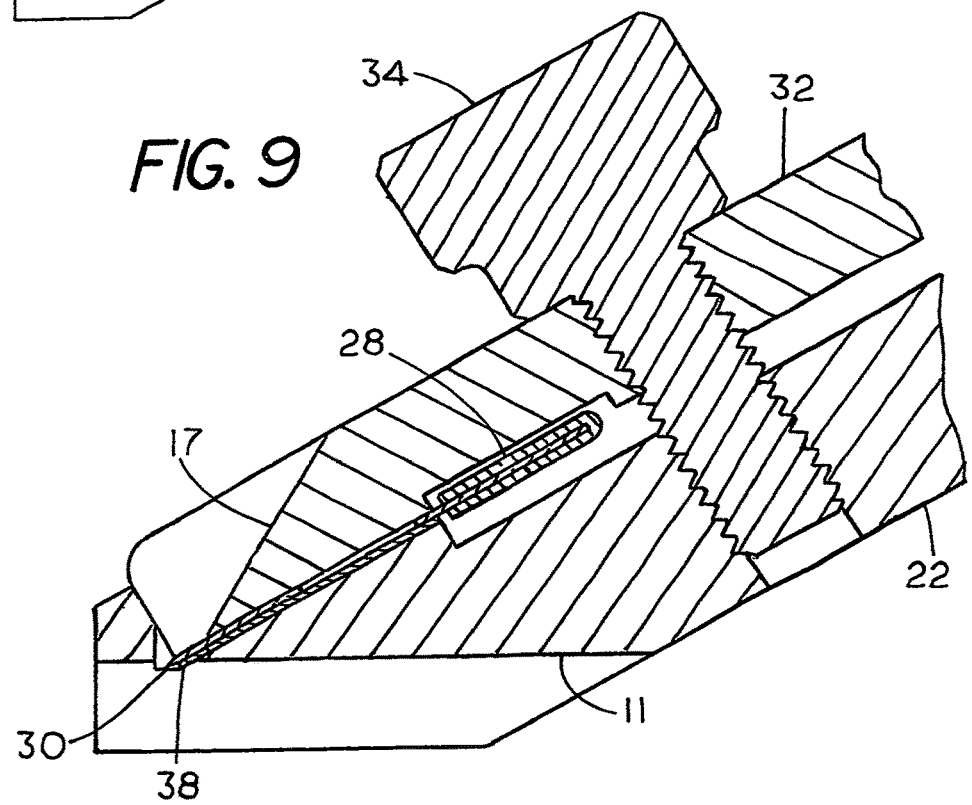
FIG. 9 is an enlarged, detail view of a portion of FIG. 8.
Figure 10:
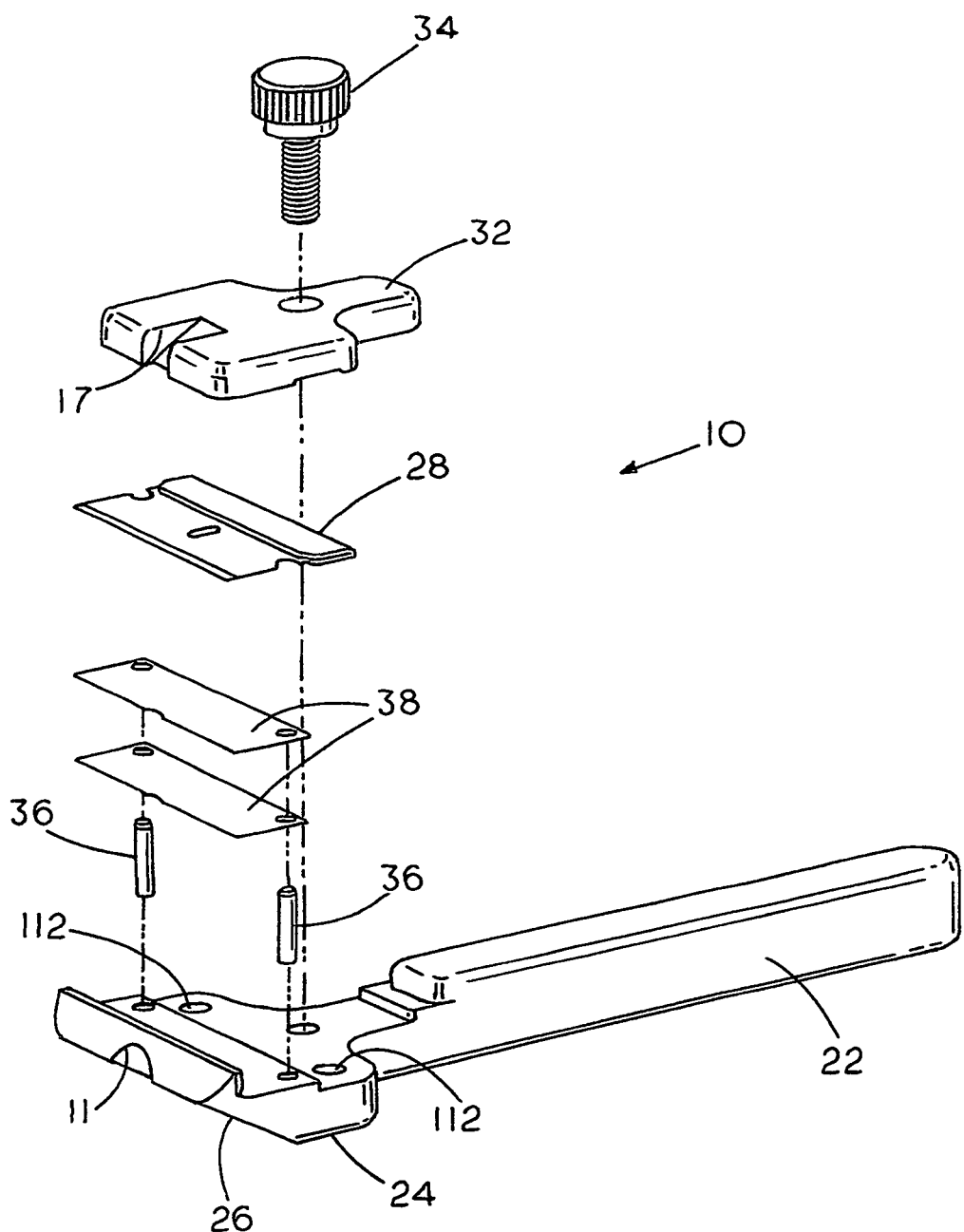
FIG. 10 is an exploded view of the skiver herein.

A blade 28 is disposed in a transverse recess in the top of the front end of handle 22, the middle front portion of which top recess intersects bottom recess 11, forming a small opening 30. The cutting edge of blade 28 extends into the opening 30, as best seen in FIG. 9. As shown, blade 28 can be a single edge safety razor of the type used in shaving, although other types of blades could also be used, if desired.

The blade 28 is preferably set at an angle of about 30 degrees from horizontal as shown, plus or minus about three degrees.

The blade 28 is secured beneath a removable cover 32 by a thumb screw 34 to the front end of handle 22 so that it can be replaced as necessary. A pair of laterally spaced apart dowel pins 36 are provided in the op recess for accurate alignment of blade 28.

The depth of extension of blade 28 into the opening 30, and thus the depth and width of the cut can be adjusted by means of shims 38, two of which are shown for purposes of illustration, although any suitable number can be used. The shims 38 can be made from stainless steel or any other suitable material in thicknesses of three or four thousandths of an inch each. See FIGS. 9 and 10. Therefore, depending upon the thickness of outside material 12, the blade 28 can be set precisely to remove material to a depth of five to fifteen thousandths or more. This comprises a significant feature of the present invention.

Figure 11:
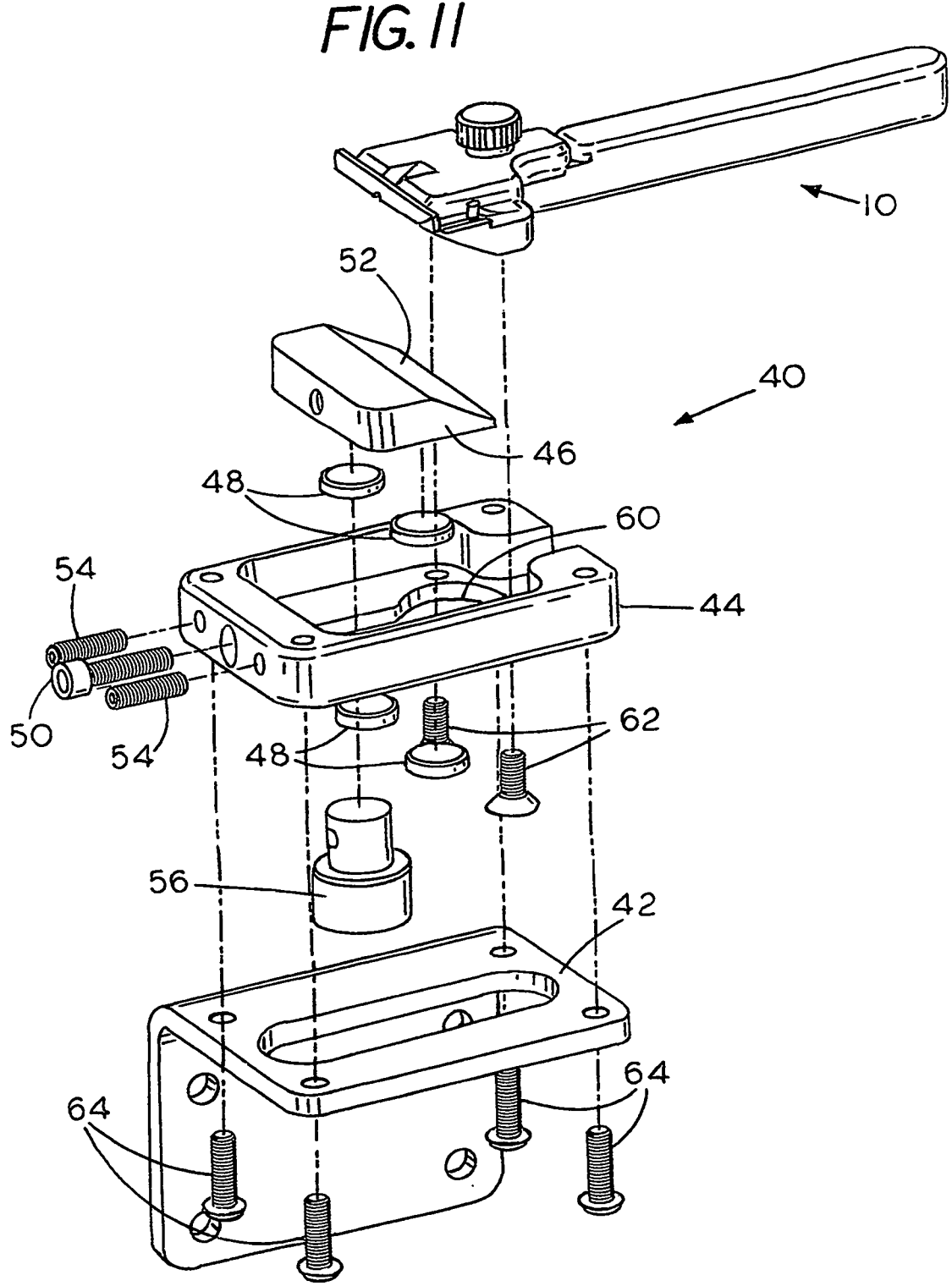
FIG. 11 is an exploded view of an optional handheld mount and an optional wall mount for use with the skiver herein.

FIG. 11 shows an optional way of using skiver 10 instead of directly on a work surface 20. A separate mount 40 is shown which can be either handheld or placed in a bracket 42 attached to a wall or the side of a table. The mount 40 includes a generally rectangular hollow base 44. A sidable jaw 46 is provided in an opening in the top of base 44, biased upwardly by magnets 48 towards skiver 10 seated therein. Longitudinal positioning of jaw 46 is controlled by a bolt 50 extending through the end of mount 40, which is threaded into one end of the jaw. The other end of jaw 46 has an angled flat surface 52 complementary to surface 26 of handle 22. Optional set screws 54 are also provided for setting the maximum gap between surface 52 and skiver 10 when the catheter 14 is advanced therebetween.

Also, a release button 56 is threadedly engaged to the bottom of jaw 46 through a keyhole slot 60 in the bottom of mount 40 as shown, so that the jaw can be removed after unscrewing bolt 50, loosening button 56 and then sliding the jaw over the large end of keyhole slot 60 so that it can be lifted out.

After the blade depth has been adjusted as desired, the skiver 10 can then be secured within mount 40 by bolts 62 before being secured to bracket 42 by bolts 64, as desired.

Figure 12:
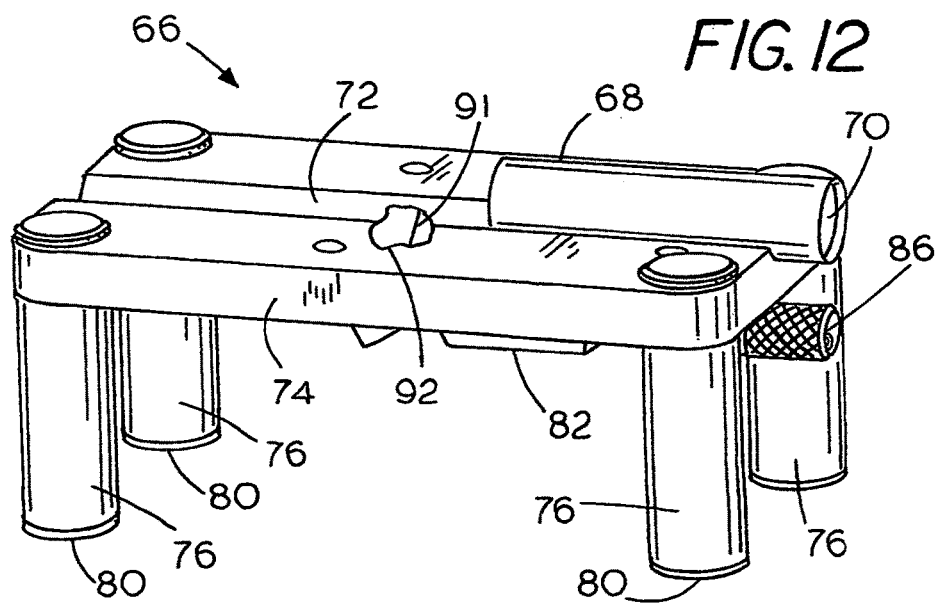
FIG. 12 is a perspective view of the improved skiver according to a second embodiment of the invention herein.
Figure 13:
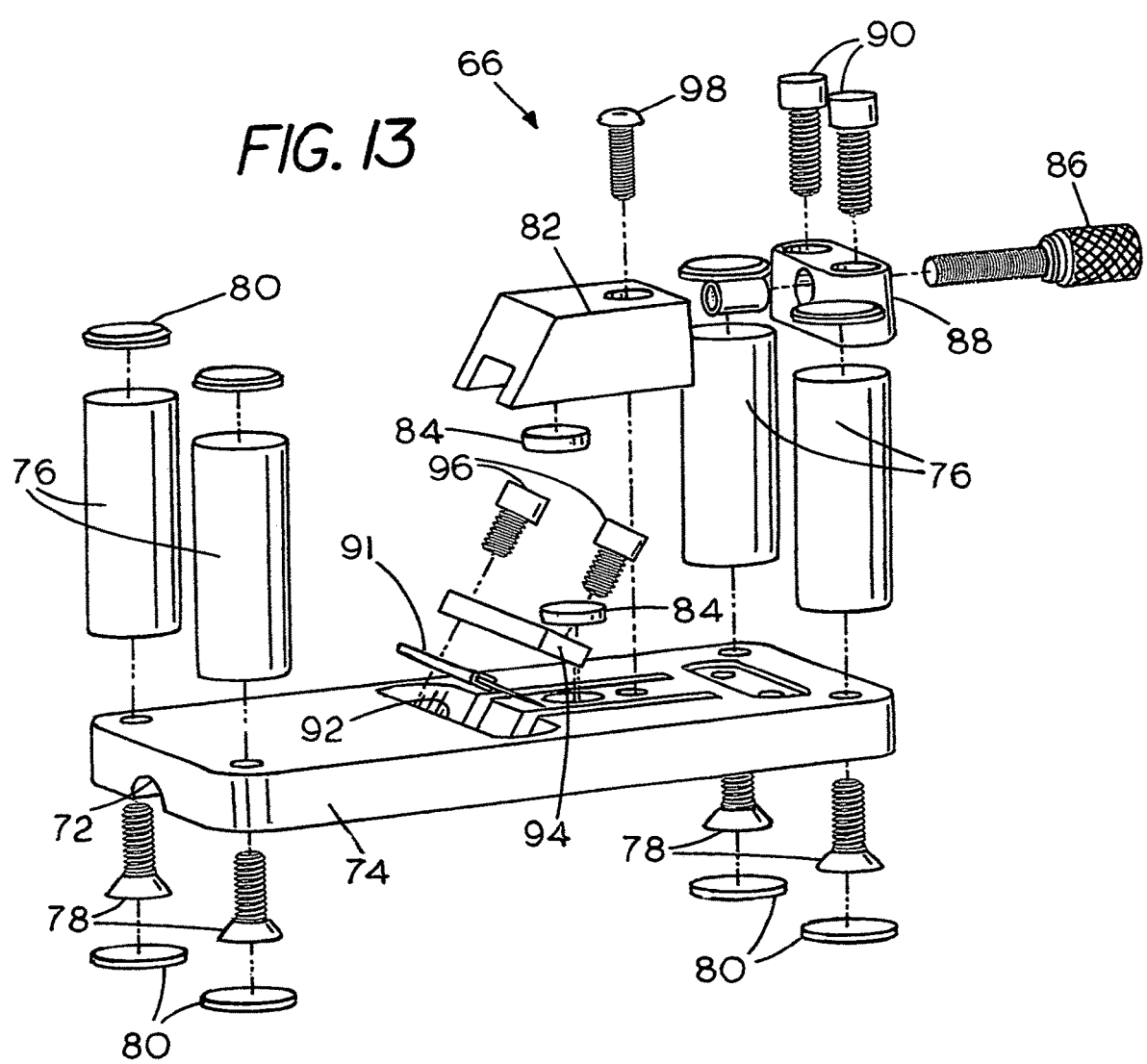
FIG. 13 is an inverted, reverse exploded view thereof.

FIGS. 12 and 13 show a skiver 66 incorporating a second embodiment of the invention for removing a thin layer of plastic heat shrink material 68 from the outside of a relatively short elongate device, such as a battery 70. In this embodiment, the elongate product or battery is slidable along a semi-cylindrical top recess 72.

Skiver 66 includes a raised body 74 supported on legs 76 secured thereto by screws 78. Rubber feet 80 are provided on at least the bottom ends of legs 74.

The underside of body 72 includes a slidable adjustment block 82 guided within recesses and biased by magnets 84, as shown in FIG. 13. A screw 86 is provided for fine adjustment. Screw 86 extends through a block 88 secured by bolts 90 to the bottom of body 74.

A blade 91 is provided on the angled side of an opening 92 extending through body 74, held in place by a cover 94 secured with screws 96. A portion of opening 92 intersects with the longitudinal recess 72. With screw 86, the blade 92 and cover 94 can be set in the desired position with the edge of the blade extending though opening 92 and into recess 70, after which the adjustment block 82 is locked in place with screw 98.

Again, blade 91 is preferably set at an acute angle of about 30 degrees of inclination so that battery 70 can then be advanced across skiver 66 to quickly cut a longitudinal slot in the heat shrink material 68 and thus facilitate its removal from the battery.

Figure 14:
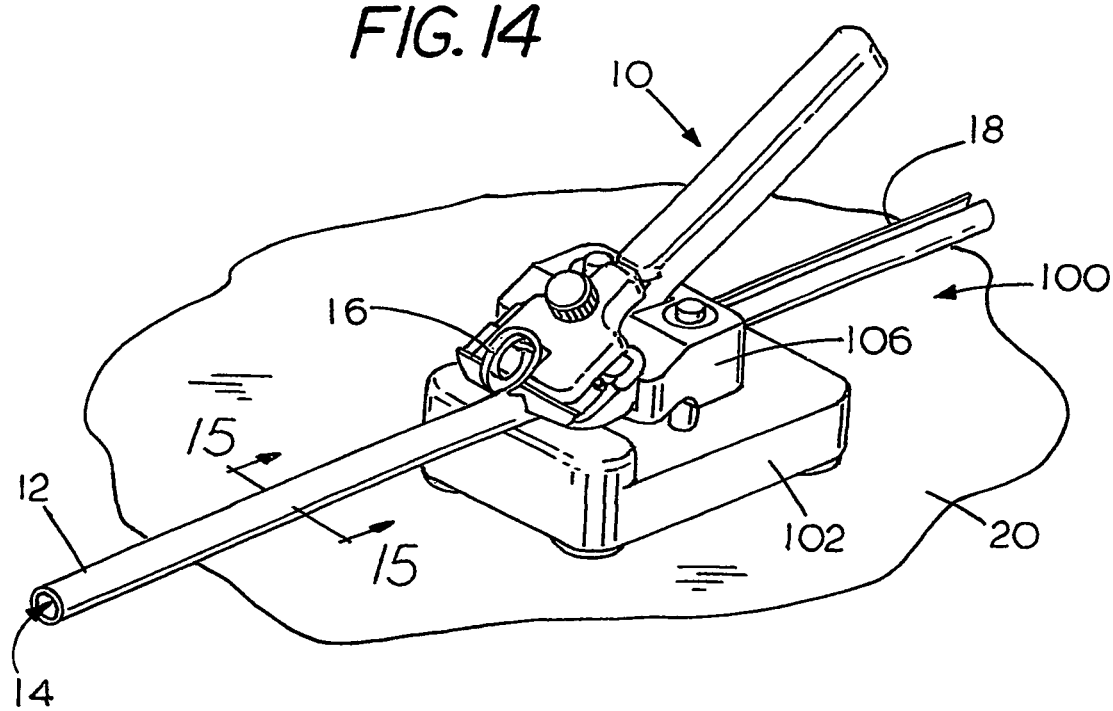
FIG. 14 is a perspective view showing an optional table mount for use with the skiver herein.
Figure 15:
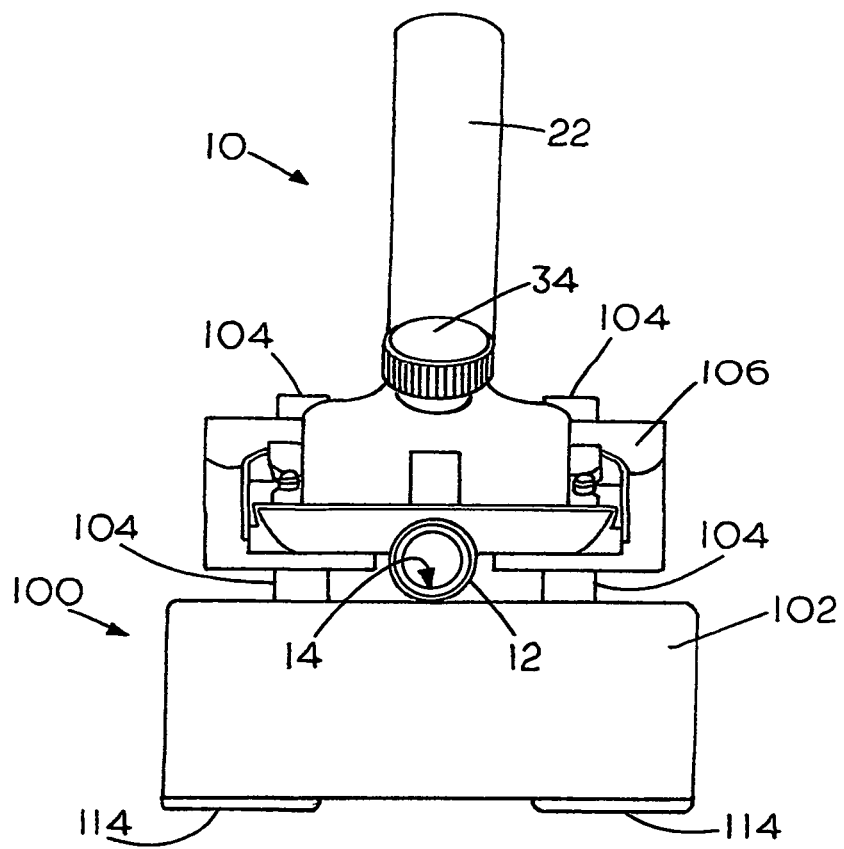
FIG. 15 is an enlarged cross-sectional view taken along lines 15-15 of FIG. 14 in the direction of the arrows.
Figure 16:
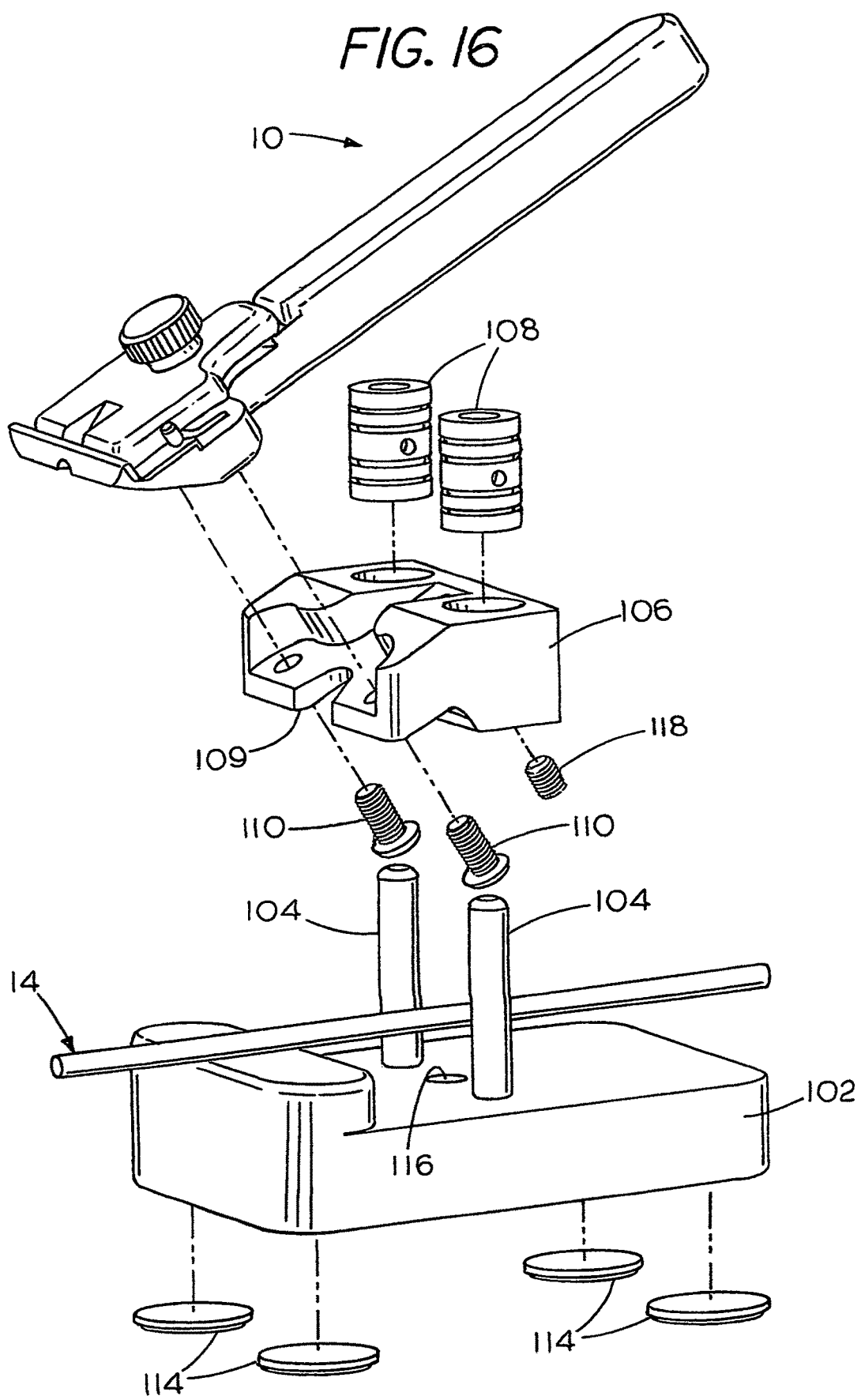
FIG. 16 is an exploded view of an optional table or bench mount.

FIGS. 14-16 show another optional way of using skiver 10 instead of directly on a work surface 20. The shiver 10 can be used with a mount 100 that includes a generally rectangular body 102 with a raised step at one end. A pair of upright pins 104 are provided on the top of body 102 behind the front step for slidably supporting a block 108 with linear bearings 108 therein on the mount body.

A longitudinal recess 109 is provided in the underside of block 108 for receiving the catheter 14.

Figure 7:
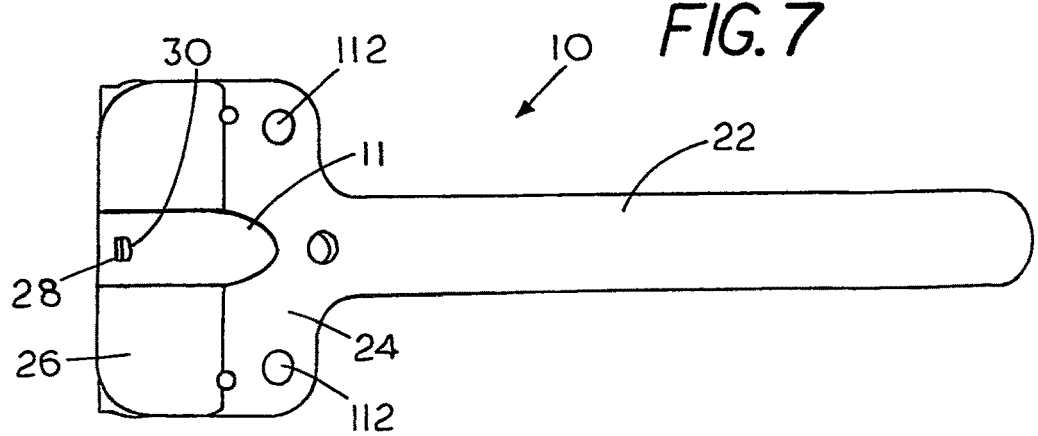
FIG. 7 is a bottom view thereof.
Figure 8:
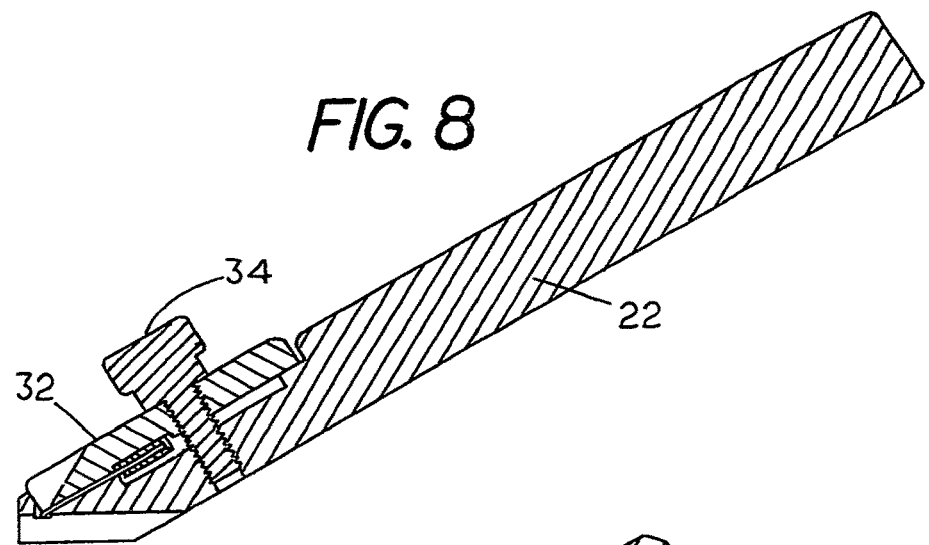
FIG. 8 is a cross-sectional view taken along lines 8-8 of FIG. 3 in the direction of the arrows.

The shiver 10 is threadedly secured to block 106 by screws 110 extending upwardly through openings in the block into holes 112 in the underside of the skiver, as best shown in FIG. 7, for secure positioning as the catheter 14 is advanced between the skiver over body 102 and underneath block 106 of mount 100.

Rubber feet 114 are preferably provided on the bottom of body 102 to resist sliding of the mount 100. An optional hole 116 can also provided to facilitate positively securing mount 100 to work surface 20 with a bolt (not shown) or the like, if desired.

A set screw 118 is provided for fine adjustment of the angle of the skiver 10 when used with mount 100. The set screw 118 extends upwardly through an opening in block 106 into engagement with the underside of skiver 10 after attachment to the block.

From the foregoing, it will be appreciated that the present invention comprises an improved skiver having several advantages over the prior art. The skiver herein is adjustable and precise. It facilitates removal of thin material from the outside of a product while minimizing if not avoiding possible damage to the product and/or injury to the user. It can also be used to cut a precise longitudinal slot in the wall of a product. The skiver herein can be handheld, or used with a separate mount. Other advantages will be apparent to those skilled in the art.

Although particular embodiments of the invention have been illustrated in the accompanying Drawing and described in the foregoing Detailed Description, it will be understood that the invention is not limited only to the embodiments disclosed, but is intended to embrace any equivalents, modifications and/or rearrangements of elements falling within the scope of the invention as defined by the following Claims.

What is claimed is:

1. A manual skiver, which comprises:
   a body having front and back ends and top and bottom surfaces;
   the bottom surface of said body being substantially planar adjacent to the front end thereof;
   said body including a longitudinal recess of predetermined cross section in the bottom surface thereof;
   said body including an opening extending between the top and bottom surfaces thereof and intersecting the recess of said body;
   a blade disposed in the body, the blade comprising a cutting end comprising a cutting edge, the cutting edge disposed in the opening;
   a shim adjacent to the blade, the shim comprising a notch positioned in the opening; and
   a removable cover comprising a bottom surface comprising a first end and a second end, the first end positioned over the cutting end and securing the blade.

2. The manual skiver of claim 1, the bottom surface of the cover comprising a first surface and a second surface offset from the first surface, the second surface positioned over the blade and spaced apart from the blade.

3. The manual skiver of claim 1, the shim positioned under the cutting end.

4. The manual skiver of claim 1, the body comprising pins on the top surface, the blade comprising cavities aligned with the pins.

5. The manual skiver of claim 1 further comprising an opening in the first end of the removable cover that allows skived material to exit the manual skiver.

6. The manual skiver of claim 1 wherein the predetermined cross section is a semi-circle.

7. A manual skiver, which comprises:
   a body having front and back ends and top and bottom surfaces;
   the bottom surface of said body being substantially planar adjacent to the front end thereof;
   said body including a longitudinal recess of predetermined cross section in the bottom surface thereof;
   said body including an opening extending between the top and bottom surfaces thereof and intersecting the recess of said body;
   a blade disposed in the body, the blade comprising a cutting end comprising a cutting edge, the cutting edge disposed in the opening; and
   a removable cover comprising a bottom surface comprising a first end and a second end, the first end positioned over the cutting end and securing the blade;
   further comprising a mount, comprising:
   a base;
   side walls extending around the base with an opening at the rear of the base; and
   a slidable jaw positioned within the side walls at the front of the base;
   wherein the manual skiver is positioned between the slideable jaw and the rear of the base.

8. The manual skiver of claim 7 wherein a rear facing surface of the slidable jaw is sloped.

9. The manual skiver of claim 8 further comprising a magnet positioned in the base.

10. A skiver comprising:
    a body comprising a top surface and a bottom surface, the bottom surface comprising a longitudinal recess, the top surface defining a blade recess, the body comprising an opening between the longitudinal recess and the blade recess;
    a blade oriented in the blade recess, the blade comprising a cutting edge, a portion of the cutting edge positioned in the opening;
    a shim adjacent to the blade, the shim comprising a notch positioned in the opening; and
    a cover attached to the body, the cover comprising a lower surface;
    wherein the top surface of the body and the lower surface of the cover secure the blade directly adjacent to the cutting edge.

11. The skiver of claim 10, the body comprising an alignment pin, the shim engaging the alignment pin.

12. The skiver of claim 11, the blade comprising a notch, the alignment pin oriented in the notch.

13. The skiver of claim 11, the body comprising a second alignment pin, the cover positioned between the alignment pin and the second alignment pin.

14. The skiver of claim 10, the top surface of the body and the lower surface of the cover securing the blade at a first location to a first side of the opening and at a second location to a second side of the opening.

15. The skiver of claim 10, the opening comprising a body opening, the cover comprising a cover opening, the cover opening aligned with the body opening.

16. The skiver of claim 10, the blade recess comprising a first portion and a second portion offset from the first portion.

17. The skiver of claim 16, the blade comprising a back portion opposite the cutting edge, the back portion oriented in the second portion of the blade recess.

18. The skiver of claim 10, the lower surface of the cover comprising a first portion and a second portion offset from the first portion, the first portion contacting the blade, the second portion positioned over the blade and spaced apart from the blade.

* * * * *